(12) United States Patent
Nüesch (10) Patent No.: US 7,766,866 B2
(45) Date of Patent: Aug. 3, 2010

(54) MILK PUMP

(75) Inventor: Hansueli Nüesch, Remetschwil (CH)

(73) Assignee: Trimed AG, Triesen (LI)

( * ) Notice: Subject to any disclaimer, the term of this patent is extended or adjusted under 35 U.S.C. 154(b) by 113 days.

(21) Appl. No.: 12/071,570

(22) Filed: Feb. 22, 2008

(65) Prior Publication Data

US 2008/0281262 A1 Nov. 13, 2008

(30) Foreign Application Priority Data

May 8, 2007 (EP) .................................. 07107683

(51) Int. Cl.
*A61M 1/06* (2006.01)
(52) U.S. Cl. .................................................. 604/74
(58) Field of Classification Search ............. 604/73–76, 604/346, 355
See application file for complete search history.

(56) References Cited

U.S. PATENT DOCUMENTS

| 3,911,920 | A | * | 10/1975 | Susinn .................... 604/75 |
| 4,929,229 | A | | 5/1990 | Larsson |
| 5,843,029 | A | | 12/1998 | Bachman et al. |
| 6,042,560 | A | | 3/2000 | Niederberger |
| 6,270,474 | B1 | | 8/2001 | Nuesch |
| 6,290,671 | B1 | | 9/2001 | Niederberger |
| 6,652,484 | B1 | | 11/2003 | Hunckler et al. |
| 6,749,582 | B2 | * | 6/2004 | Britto et al. .................... 604/74 |
| 2003/0204164 | A1 | * | 10/2003 | Britto et al. .................... 604/74 |
| 2004/0024351 | A1 | * | 2/2004 | Greter et al. .................... 604/74 |
| 2004/0087898 | A1 | * | 5/2004 | Weniger .................... 604/74 |
| 2004/0199107 | A1 | | 10/2004 | Nuesch |

FOREIGN PATENT DOCUMENTS

| EP | 1 195 170 | 4/2002 |
| WO | WO 01/34226 A1 | 5/2001 |

OTHER PUBLICATIONS

European Search Report Application/Patent No. 07107683.0-1257 dated Aug. 29, 2007.

* cited by examiner

*Primary Examiner*—Nicholas D Lucchesi
*Assistant Examiner*—Leah Stohr
(74) *Attorney, Agent, or Firm*—Buchanan Ingersoll & Rooney PC (57) ABSTRACT

A milk pump for pumping milk from a woman's breast comprises a breast hood for receiving tightly a woman's breast. Furthermore, there is a milk collecting arrangement for receiving milk pumped from said woman's breast. This milk collecting arrangement includes a support and a downwards directed opening in the support for providing a suction communication to the breast hood. Moreover, the milk collecting arrangement comprises a manual pumping unit above the said opening. The manual pumping unit includes a wall forming and surrounding a displacement space which comprise a front wall and a peripheral wall extending in longitudinal direction. A suction device is displaceable inside the displacement space to provide suction through the opening, wherein the displacement is provoked by an actuation device. Furthermore, there is a latching arrangement for releasably connecting at least part of the wall of the displacement space to the support for an easy exchange.

29 Claims, 5 Drawing Sheets

MILK PUMP

FIELD OF THE INVENTION

The present invention relates to milk pumps for pumping milk from a woman's breast. Conventional milk pumps of this kind comprise a breast hood for receiving tightly a woman's breast to draw milk out of it and to collect it first in a milk space from which it flows, mostly over a non-return valve, into a collecting receptacle or bottle. The part of the milk pump, which joins the breast hood, includes normally a support of any shape and design to carry a manual pumping unit above an opening to the milk collecting space so that suction can be exerted by the manual pumping unit through this opening which is a downwards directed in the support for providing a suction communication to the breast hood. This suction communication is necessary for a manual pumping unit above the opening which includes a wall forming and surrounding a displacement space. The displacement space defines a longitudinal axis along which a suction element is moving, be it a piston or a membrane. The wall, thus, has a front wall of the displacement space and a peripheral wall which extends in longitudinal direction (or direction of suction movement) of the displacement space. For this movement, an actuator is provided, which may be a slider or a lever for mechanically displacing the suction element substantially in axial direction of the longitudinal axis.

BACKGROUND OF THE INVENTION

Such a milk pump has, for example, become known from U.S. Pat. No. 6,749,582. In this milk pump, the support is about tubular, the displacement space (and its walls) being able to be plugged into the upper opening of the tube in from above. As far as the displacement space is merely plugged, the interconnection of these parts is, of course, quite unreliable. In a similar way, U.S. Pat. No. 6,652,484 shows a milk pump where a cylindrical displacement space of a manual pumping unit in the shape of a syringe can be screwed off. Also in this case, there is an alternative for connecting a suction hose instead.

In both cases, pumping is rather troublesome; in the first case due to the mere plug connection and the necessity to move a suction membrane upwards, while a cranked actuation lever has to be moved in lateral direction (which leads to friction losses and causes fatigue of the hand); in the second case, because actuating a syringe in two opposite directions requires the use of both hands for pumping, while the milk receptacle has to be held too. Hose connections, however, should be avoided because of the possibility of an entanglement, because of the difficulty to keep it in hygienic conditions, and also because of the tendency of the resilient material of such hoses to become brittle, crumbling or flawy.

Now, a glance should be thrown to the fact, why at all such a releasable connection between the walls of the displacement space and the support is usually made. One reason is the possibility of cleaning separately all pump elements, or in other words to meet higher hygienic standards. Another reason, however, is in both above cases, that one should provide a possibility to use selectively (at least) two types of pumps driven by physical strength. It has been mentioned above that a hose connection is not favorable; however, a screwing connection has also its perils: First removing from a mold during production, e.g. by injection molding, is easy, particularly because the threaded portion, due to the necessary seal, has to be relative long. This leads to higher costs. But the necessary long screwing in practical use is awkward and may, if the two threaded parts are engaged in a wrong manner, lead easily to stripping the thread, which would make the thing unusable. Moreover, screwing does not the use of a curved displacement space for a piston, as is known from WO 01/34226, where the displacement space is integrated into a cap-like support, thus impeding separate cleaning or any exchange of the pumping system, while involving restrictions in the choice of material which should meet both requirements, i.e. that of sufficient strength and that of low friction for the piston, or for a membrane or any other suction member.

A combination of a releasably attachable displacement space and of a support (which, in principle, may be formed in any way desired) permits, however, in an advantageous manner that different types of milk pumps may be brought onto the market, which have all the same support which, in this way, may be produced in greater quantities at reduced costs. Also in this respect, a screw connection would be disadvantageous, because it requires more expenditure of labour when assembling the parts. On the other hand, there existed good reasons why no other connections have been suggested up to now, i.e. because the pumping motion exerts a certain longitudinal force in the direction of movement to the displacement space, thus necessitating a connection as stable as possible. However, the connection should not be so that, when cleaning the parts, the user is hardly able to detach the parts from one another.

SUMMARY OF THE INVENTION

Therefore, it is an object of the invention to design a milk pump of the type mentioned at the outset in such a way that it may easily be handled both when pumping and when cleaning.

This object is achieved according to the invention by a latching arrangement for releasably connecting at least part of the wall, which defines the displacement space, i.e. the front wall and/or the peripheral wall, to the support for easy exchange.

Using a releasable connection by a latching a lathing element, the following advantages are obtained:

- Although the at least one part of the wall of the displacement space is firmly connected to the support, while pumping, it can be released by a single grasp for cleaning purposes;
- During fabrication, this wall part or the whole displacement space can be simply put onto the support where it is latched then;
- The displacement space or its peripheral wall can be produced from a material which enhances sliding, whereas the support has only a supporting function and could be made of a different material;
- Any replacement of the displacement space, e.g. for repair, can easily be made;
- A releasable connection to be latched by a latching element can be easily be formed, for example by injection molding, which has a positive effect also to the production costs;
- A releasable connection to be latched by a latching element does not have narrow screw threads which are difficult to clean.

For facilitating pumping, it is advantageous, if the displacement space is arcuate in correspondence with the bow of movement of a pivoting lever, which forms the actuation device, because in this way the transfer of movement is free of friction to a large extent.

However, in such a case, the displacement space can only be put onto the support in a single predetermined direction, so that the centers of the arcuate displacement space and of the pivoting movement coincide. Therefore, it is particularly preferred, if a securing device against torsion is provided. A favorable embodiment will be described later with reference to the drawings.

If the latch connection is located at the side near to the opening, which leads to the collector receptacle or bottle, fastening is secured in a manner free from any play just at that place, where the transition of the sucking flow should happen free from any leakage.

Having separated the support from the displacement space (in comparison with the approach according to WO 01/34226), it is now possible, to adapt the material better to different requirements. For this reason it is preferred, if the displacement space is formed from a material different from that of the support. In particular, the material of the displacement space has a smaller friction coefficient than the material of the support and/or the material of the support has a greater strength or hardness than the material of the displacement space. For example, the displacement space may be produced from a polyethylene (PE) or from polyamide (PA), and/or the support may be manufactured from a polycarbonate (PC) or from a polypropylene (PP).

BRIEF DESCRIPTION OF THE DRAWINGS

Further details of the invention will become apparent from the following description of embodiments schematically illustrated in the drawings, in which

FIG. 2 is a perspective exploded view of the milk pump according to FIG. 1, to which FIGS. 3 and 4 illustrate respective units to be mounted each as a module either for a fixed relative position of the breast hood and the actuation lever, or for an adjustable relative position;

FIG. 5 is a rear view corresponding to the arrow V of FIG. 2;

DETAILED DESCRIPTION OF THE DRAWINGS

Figure 1:
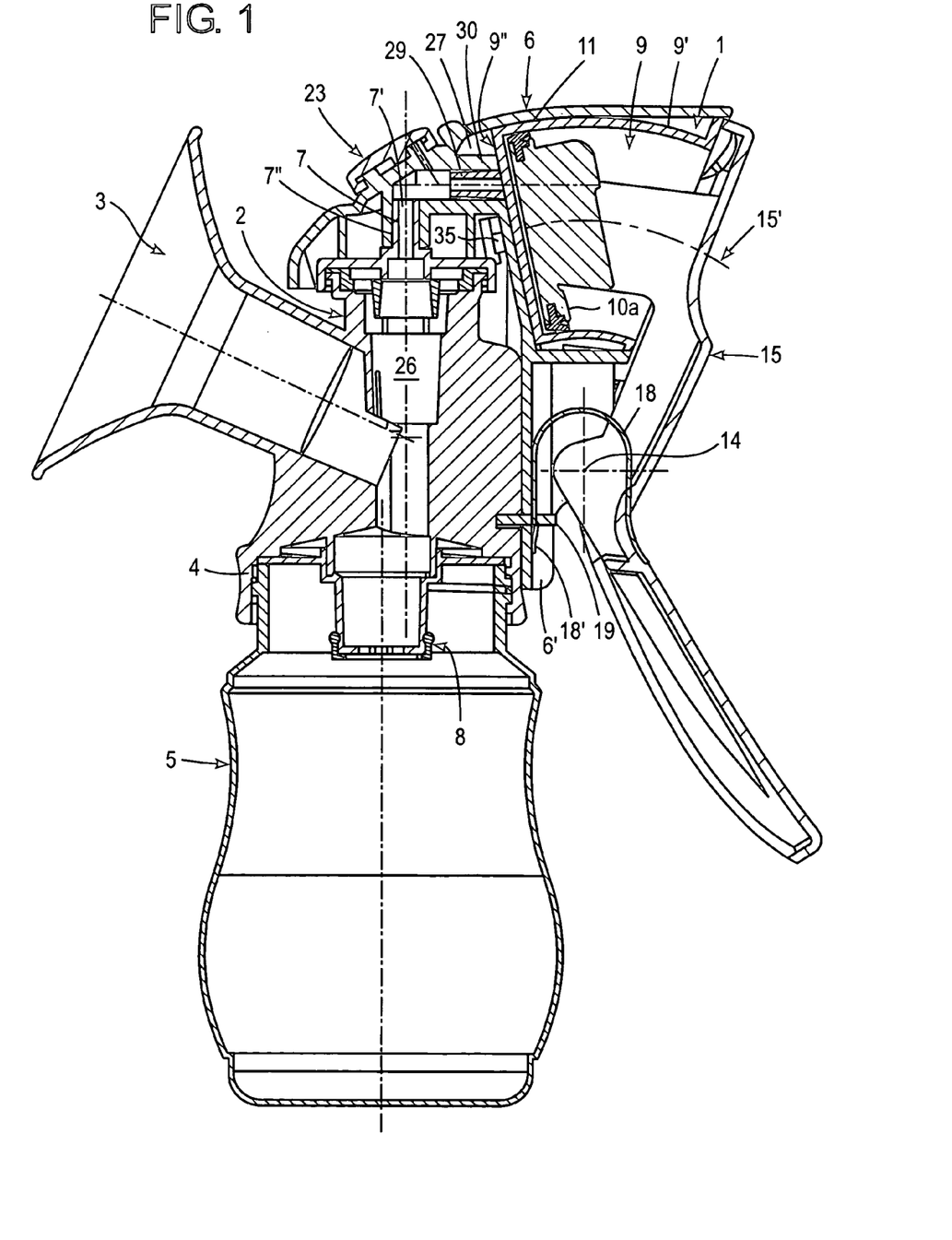
FIG. 1 is a vertical cross-section about along the line I-I of FIG. 5 of a first embodiment of a milk pump according to the invention.

The milk pump illustrated in FIG. 1 comprises an upper support 6 including a manual pumping unit 1, which is plugged onto a connection piece 2. To this end, the connection piece 2 comprises a pipe socket 7, which extends in upward direction and has a connection opening 7' onto which a pipe socket 7" of the support is plugged. The two pipe sockets 7, 7" are slightly conical so that a tight and firm connection will be established. The support 6, in principle, could be constructed in a variety of shapes and manners, and could, for example, consist of individual bars or strips; however, it is preferred, as illustrated, if it is about cap-shaped, forming a hollow interior where it receives and protects the manual pumping unit 1.

The connection piece 2, on the one hand, comprises a breast hood 3 or horn, and a threaded part 4, on the other hand, by which the pump may be screwed onto a milk collector receptacle 5. In a known manner, there is a non-return valve 8 between the milk collector receptacle 5 and the connection piece 2. This non-return valve is preferably constructed as is described in U.S. Pat. No. 6,270,474, the content of which should be incorporated here be reference.

At the upper side of the support 6, a known regulator knob 23 may be provided, which regulates the supply of secondary air and, thus, the force to be applied when pumping. A particularly preferred embodiment of such a regulating device is described, for example, in U.S. Pat. Nos. 6,042,560 and 6,290,671, the content of which should also be incorporated here be reference.

In order not to make cleaning of the manual pumping unit 1 more difficult by the access of mother milk to it, an overflow valve 26 is pre-posed to the opening 7'. This overflow valve is preferably designed in such a manner as is described in EP Patent No. 0 121 825, the content of which should be incorporated here be reference.

Figures 2, 3, 4, 5:
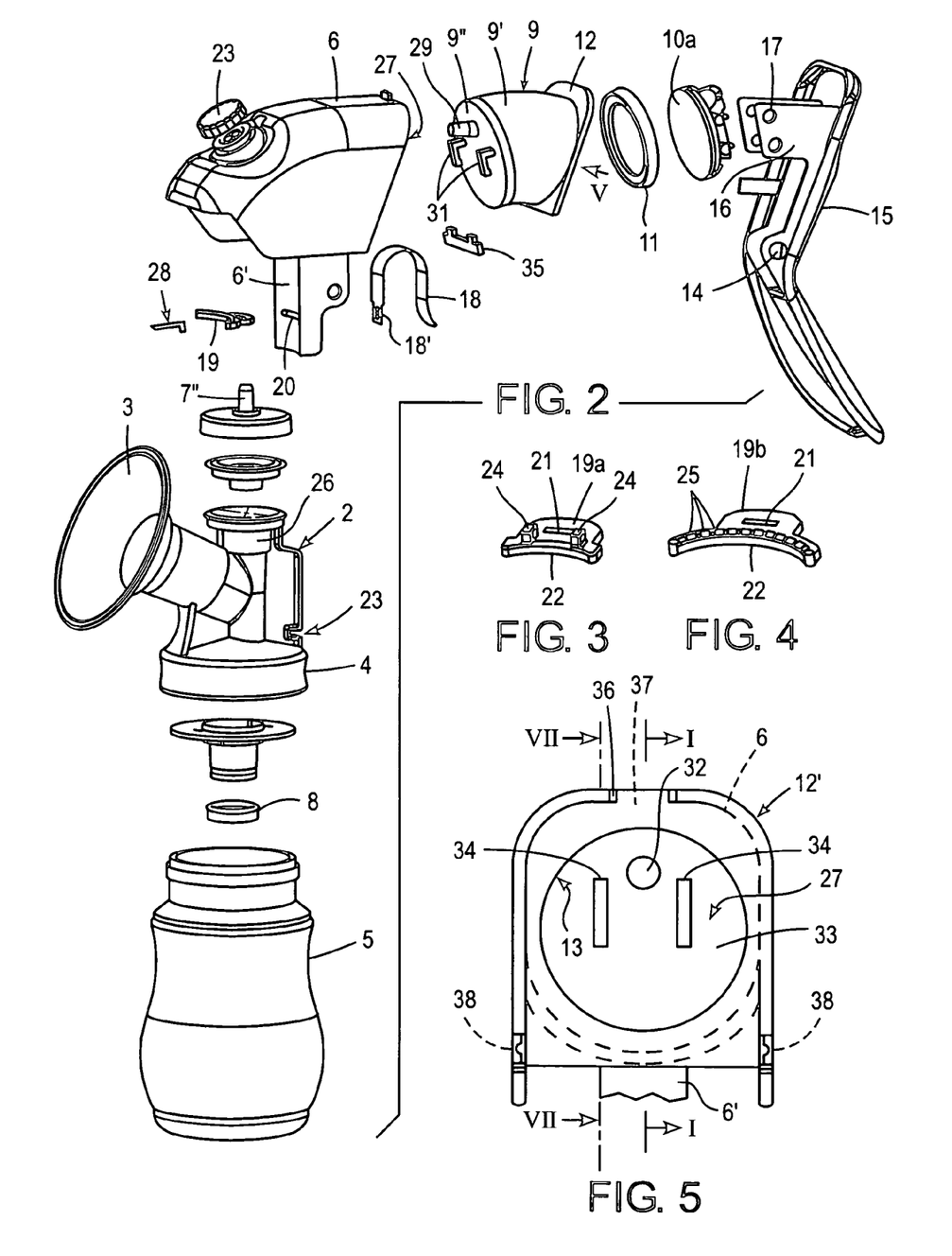

Within the cap-shaped support 6 is a cavity 27 which receives the pumping unit 1 including its displacement space 9. The displacement space 9 is surrounded by a peripheral wall 9' and is closed towards the opening 7' by a front wall 9". This displacement space 9, as particularly illustrated in FIG. 2, is inserted, to be protected, into the cap-shaped support 6, which has a substantially four-cornered cross-section with rounded corners (see also FIG. 5), and is releasably connected to it. Since a piston 10a as a suction member should be moved to and for within the displacement space 9 by an actuating member or (two-armed) lever 15, which pivots about a pivot point 14, the curvature of movement 15' should coincide with the curvature of the peripheral wall 9' and with the curved extension of the displacement space 9, as best as is possible, because otherwise a hand fatiguing friction will be caused. As is illustrated in FIG. 2, a shield 12, congruent to the four-cornered cross-section of the support 6, may either be inserted into the appropriately shaped cavity 27 of the cap-shaped support 6 or may be plugged onto it (see FIG. 7) in order to ensure this coincidence. As may be seen from FIG. 1, with a very precise manufacture, one could do without such an insert or such a shield 12, although it is preferred, because it acts as a securing device against any torsion of the displacement space 9 relative to the cavity 27.

Referring to a variant 12' of this frame or shield serving as a closure element illustrated in FIG. 5, this shield 12' has an opening 13 through which a guiding element 16 of the lever 15 may be moved. This guiding element 16 may be fastened to the piston 10a, surrounded by a sealing ring 11, by means of plug-in holes 17. The lever 15 is, for example, biased by a return force of a return spring 18, which preferably is a simple U-shaped leaf spring, one end of which abuts against the lever 15 (see FIG. 1). The other end 18' of the spring 18 is mounted to the support, but optionally to the connection piece 2 instead. This can be done using a connection element 19 which may, for example, be formed by a screw. In this case, the connection element 19 has a double purpose, because it attaches also the support 6 to the connection piece 2.

FIG. 2 shows a preferred embodiment, wherein a downwards extending support foot 6' comprises an, e.g. slot-like, opening 20, through which selectively an arcuated connection element, generally 19, either as an element 19a, i.e. as a locking member for locking the position of the lever relative to the support 6, or as an element 19b (vide FIGS. 3, 4) may be put through, the latter delimiting a relative rotation of the lever 15 with respect to the receptacle 5 and the support 6, but allows such rotation in part over a limited angle. This arcuated connection element 19a and 19b has each a slot 21 through which the end 18' of the spring 18, after its introduction into the slot 20, may be inserted behind this slot 20 so that the connection element 19 is locked. The forward rounding 22 of the respective connection element 19 is in a slot guidance 23 (FIG. 2) of the connection piece 2. In the case of the connection element 19a, projections 24 embrace the end limits of the slot, thus forming a fixed connection which does not permit any relative rotation of the connection piece 2 and the support 6.

Alternatively however, the connection element or delimiting element 19b can be inserted into the slot 20 and may be fastened by the end 18'. This connection element 19b is broader than the element 19a and has suitably index projections 25 which permit limited rotation of the support 6 relative to the connection piece 2, while holding it in the respective index position. In this way, an adaptation of the relative position when pumping the left breast or the right breast is possible. Through the exchangeability of the connection elements 19a and 19b, it is possible to adapt the function of the pump to the wishes of the user, and different types of the manual pump, as shown, may easily be fabricated without changing the necessary molds too much. It will be understood that this exchangeability is conceivable independently of whether the displacement space 9 or at least one wall of it is exchangeable or not so that these exchangeable connection elements 19a, 19b constitute a separate invention.

It will also be understood that the two parts 19a, 19b may be formed in various ways and may be provided either on the support 6 or its foot 6' (so that it cooperates with limiting surfaces or a counter-latch of the connection piece 2, for example in the way of the leaf spring 28 and the indexing counter-nub of FIG. 1), or on the connection piece 2 to cooperate with limiting surfaces or a counter-latch on the support foot 6'. The index projections, instead of being formed on the upper surface, could be formed, for example, on the front side of the element 19b opposite to the connection piece 2 or opposite to the support 6. Finally, one could optionally even do without the index projections 25 and could solely provide spaced projections (corresponding to the projections 24), but this is less preferred.

Concerning the exchangeability of the displacement space 9 just mentioned or of at least one wall 9' and/or 9", the following should be explained.

As is apparent from FIGS. 2 and 1 (or even better FIG. 7), a connecting pipe socket 29 protrudes from the front wall 9'" of the displacement space 9. According to FIG. 1, this pipe socket 29 may be plugged into a counter socket 30 on the support 6. Since both sockets 29, 30 are slightly conical, they create a sealed plug-in connection which prevents any leakage.

However, there are also two parts of a latching device which protrude from the front wall 9'" (FIG. 2) and are, in this embodiment, formed by two hooks 31. When inserting the displacement space 9 into the cavity 27 of the support 6, the pipe socket 29 enters a circular opening 32 of a receiving plate 33 (FIGS. 5, 7) of the support 6, on the one hand, but on the other hand, the hooks 31 each penetrate a slot 34 of the plate 33. Now a locking bar 35, e.g., a wedge lock which presses the front wall 9'" against the plate 33, may be slid between the hooks 31, as is particularly seen in FIG. 7. However, it will be understood that this is only one example of a possible latching arrangement, the man skilled in the art of latching arrangements knowing a variety of modifications. For example, the front wall 9'" could have lateral projections, with which a locking eccentric or a cam may cooperate to press the wall 9'" against the plate 33 as depicted in FIG. 8. As shown in FIG. 8, front wall 9'" includes lateral projections 31'. An eccentric or cam 35' is provided at both sides of the support 6 and when rotated by a knob 35" press the lateral projections 31' sealingly against the plate 33, after the pipe socket 29 has entered the opening 32 of the plate 33. When inserting the displacement space 9 into the support 6, projections 31' abut against the eccentrics or cams 35'. To bring the lateral projections 31' behind the eccentrics or cams 35', displacement space 9 is slightly turned about axis of the curvature of movement 15' so that the lateral projections 31' slide over and under (respectively) the eccentrics or cams 35' before reaching their position behind the eccentrics or cams 35' by a slight return rotation about axis of the curvature of movement 15'. In each case, however, a latching arrangement fulfills two preconditions:

It may easily and quickly be inserted or removed, and

It resists to large forces in the direction of movement of the suction member (be it a piston or a membrane), i.e. in the present case along the curvature of movement 15'.

It is clear that the location of the latching arrangement, has mentioned above, can be chosen at will. If it is chosen in the region of the peripheral wall 9', some space will, in general, be lost for the displacement space. If the location of the latching arrangement is chosen at the right-hand (with reference to the drawing), open end of the support 6, a sealed connection to the opening 7' would become difficult. Therefore, it is preferred, if the latching connection 31, 35 is situated at the side facing the opening 7' which leads to the receptacle 5, as may be seen in the drawings. Furthermore, it will be understood that it is also conceivable to form the wall 33 as the front wall of the displacement space 9 and only to latch only the peripheral wall 9' to the front wall 33 thus formed. However, in such a case, sealing would be made more difficult, and possible an about circular sealing ring would become necessary at the front side of the peripheral wall 9', where cleaning might be relative more difficult.

From EP 1 231 955, it is known to form a support in a cap-like manner, but there for a different purpose, because according to this document it forms simultaneously the peripheral limitation of the displacement space. Apart from a more difficult cleaning facility, this has the consequence that in production one has always to find a compromise, because the wall of the support is either made of a strong support material, which however results in more friction of a piston and more difficulty of moving it, or one uses an anti-friction material, which has less stability of shape. By separating the two functions in accordance with the invention, an optimum can be achieved for both requirements, or in short: the peripheral wall (at least) of the displacement space may be formed from a material which differs from that of the support 6. Suitably, one will proceed in such a manner that the material of the displacement space (or its peripheral wall) has a smaller frictional coefficient than the material of the support and/or the material of the support has a greater strength or hardness that the material of the walls of the displacement space. In practice, the walls of the displacement space will advantageously be manufactured from polyethylene (PE) or from polyamide (PA) and/or the support is produced from a polycarbonate (PC) or a polypropylene (PP).

Referring to FIG. 5, it shows also how the shield 12 may be fastened to the outer end of the cavity 27. To this end, it is mounted by means of a, preferably elastic, circumferential clasp 12' (FIGS. 5, 7) to the support cap, i.e. the clasp 12' is shifted over the rim of the cap-like support 6', in the embodiment of FIG. 1 as to hold the shield 12, in the case of the embodiment of FIG. 7 holding a rim 38 of a pot-shaped membrane 39, which will be described later. In each case, the cross-sectional shape of the cavity 27 (see also FIG. 5) which differs from a circular shape, securing against torsion (rotation) is achieved, because the arcuate displacement space 9 can only be inserted such that its curvature coincides with the arcuate movement 15' (FIG. 1).

Figure 7:
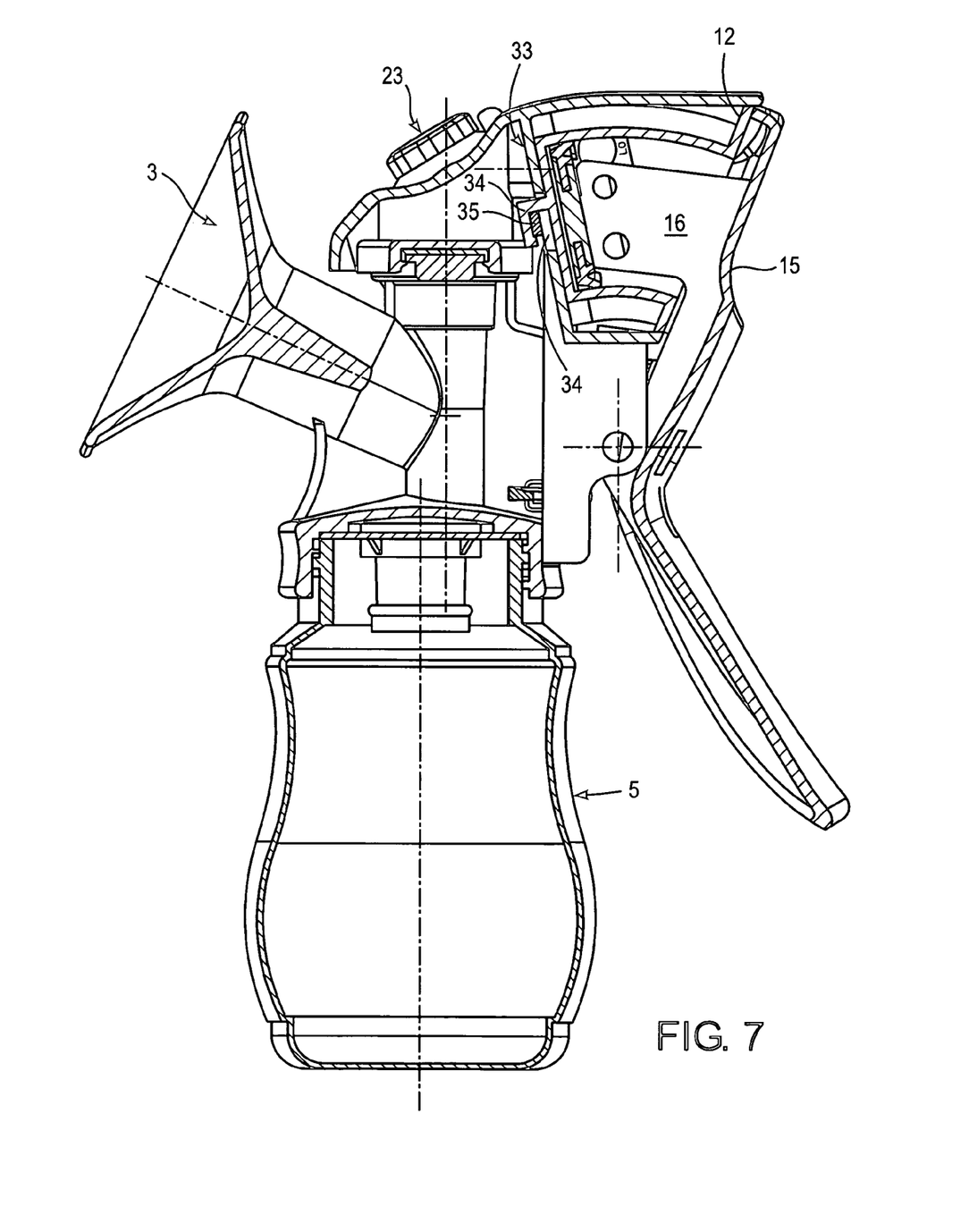
FIG. 7 shows a cross-sectional view similar to that of FIG. 1, but being offset as to extend along the line VII-VII of FIG. 5.
Figure 8:
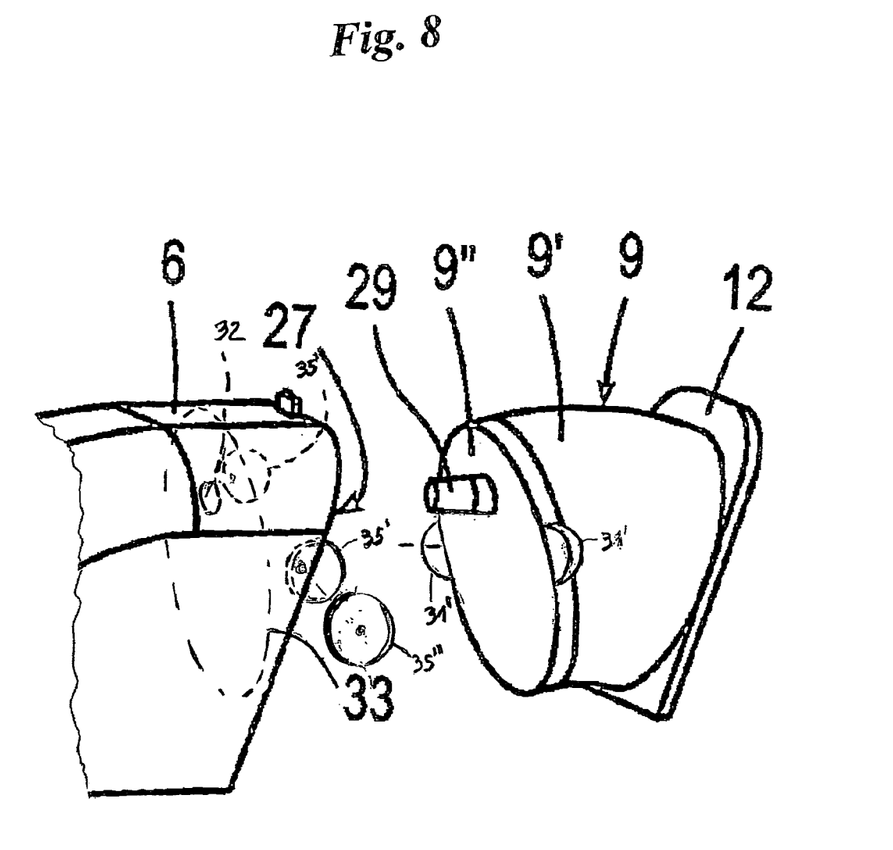
FIG. 8 is a view of another exemplary embodiment of a milk pump.

The upper side of the clasp 12' comprises a slot opening 36 which is engaged by a tab or projection 37, as may be seen from the embodiment of a support according to FIG. 7. Thus, if this clasp 12' is formed of a slightly elastic material, it can easily be drawn over the tab 37. The lower rim of the clasp 12' may be maintained by latching knobs 38.

Figure 6:
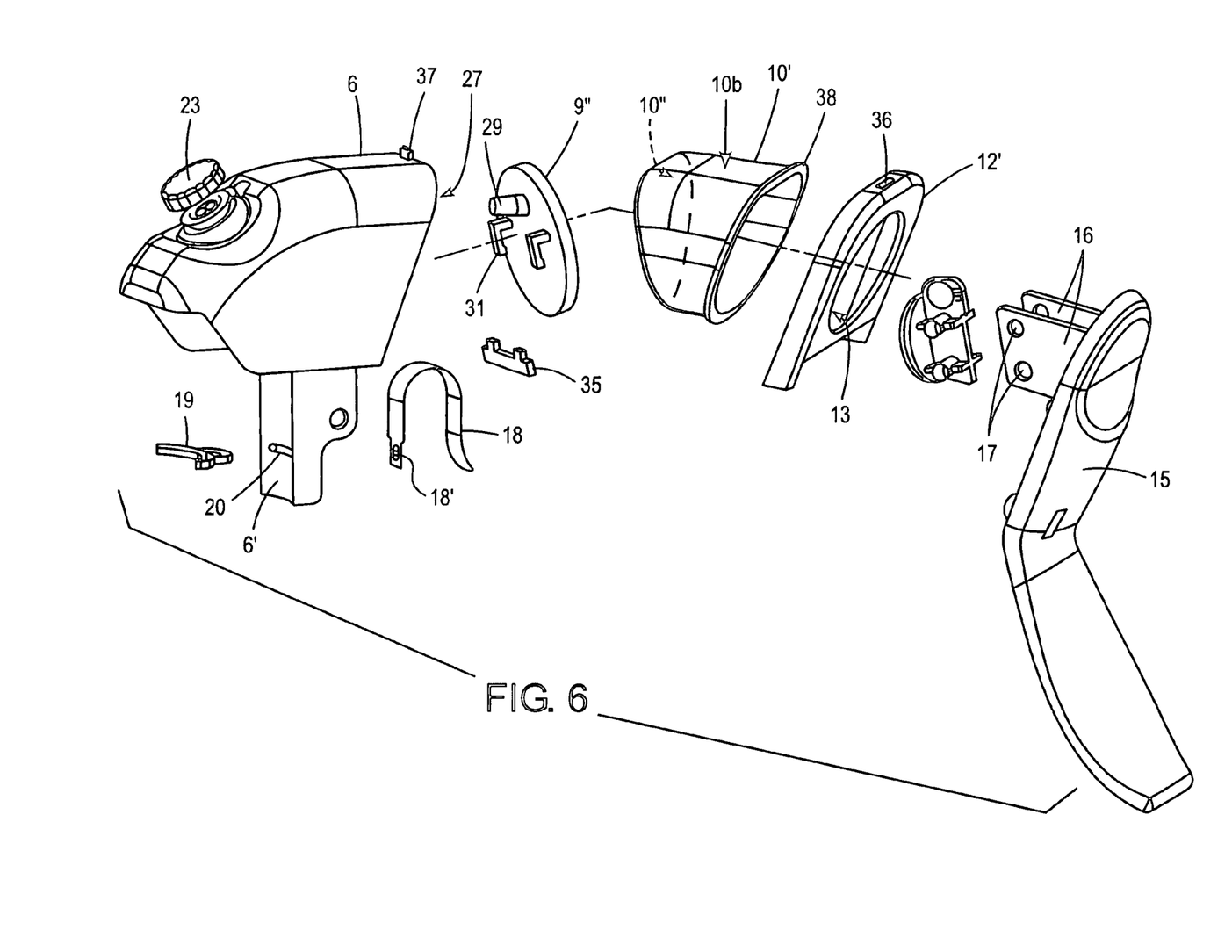
FIG. 6 is an exploded illustration, similar to FIG. 2, of another embodiment of the pump of FIG. 1, but with a different pumping unit.

With reference to FIG. 6, it should be shown, that the invention permits the production of different types of milk pumps at small expenses. Parts of the same function have the same reference numerals as in the previous figures.

The parts at the left and the right side of FIG. 6 correspond to those parts of FIG. 2 which are shown at these sides. The difference is that, instead of the piston 10a (FIG. 2), there is an about pot-shaped membrane 10b having a peripheral wall 10' and a forward directed front wall 10" indicated in dotted lines. This is preferably formed in the manner described in European Patent Application No. 07 101 346.0. To this front wall, a joining member 39 is attached which, in turn, is connected to the guiding element 16 of the lever 15 by means of plug-in holes 17 and penetrating plug-in pins. In principle, one could provide an arcuate cylindrical space in correspondence with the displacement space 9 for the pot-like membrane 10b too. However, the advantage of a releasable attachment of the displacement space 9 has already been pointed out above, the advantage, above all, residing in the possibility of an adaptation of the plastic material to the different frictional conditions When using a membrane 10b one needs not to take the friction coefficient of the material into account and, therefore, it is sufficient, if instead of the whole displacement space 9 according to FIG. 2 and its walls, it is only the front wall 9" which is inserted for covering the slots 34 and for interconnecting the pipe sockets 29 and 30 (vide FIGS. 1, 5 and 6). In contrast, it is the whole cavity 27 of the support 6 which is at disposal for accommodating the pot-like membrane 10b, i.e. its cross-section may be larger than that of the piston 10a, so that it results in a higher pumping performance. For fastening the membrane 10b to the support 6, the, preferably elastic, clasp 12' is provided, as has been already described with reference to FIG. 5, and clamps the rim 38 of the membrane 10b to the rim of the support 6 and of its cavity 27.

What is claimed is:

1. A milk pump for pumping milk from a woman's breast, comprising:
    a breast hood for receiving a woman's breast;
    a support;
    an opening in said support for providing a suction communication to said breast hood; and
    a manual pumping unit which includes
    a substantially rigid wall forming and surrounding a displacement space, said displacement space defining a longitu-dinal axis and having a predetermined cross-sectional dimension, said wall comprising a front wall of said displacement space and a peripheral wall extending in a longitudinal direction;
    a suction unit displaceable in said displacement space substantially along said longitudinal axis to provide suction through said opening;
    an actuator for mechanically displacing said suction unit substantially in an axial direction; and
    a latch formed on said front wall for releasably connecting at least part of said wall to said support wherein the latch comprises at least one protrusion from the front wall in the longitudinal direction including at least one hook and at least one cylindrical protrusion formed on said front wall and the support includes a receiving plate including respective openings for the at least one protrusion.

2. Milk pump as claimed in claim 1, wherein said actuator comprises a lever having at least one end region which runs through a pivot path when actuated.

3. Milk pump as claimed in claim 2, wherein said lever is a two-armed lever pivotally supported in its center region.

4. Milk pump as claimed in claim 2, wherein said wall including said peripheral wall is releasably connectable to said support, said peripheral wall and, thus, said displacement space having a curvature in longitudinal direction so as to correspond to said pivot path of said lever end region.

5. Milk pump as claimed in claim 4, further comprising a torsion preventing arrangement for ensuring alignment of said curvature and said pivot path.

6. Milk pump as claimed in claim 5, wherein said torsion preventing arrangement is formed as a hollow shape of said support which surrounds said wall and said displacement space, said hollow shape differing from a circular shape in cross-section, while said wall of said displacement space has a cross-sectional shape fitting into said hollow shape of said support in such a way that said alignment is ensured.

7. Milk pump as claimed in claim 6, wherein said hollow shape is substantially cornered in cross section.

8. Milk pump as claimed in claim 1, further comprising restoring means for returning and biasing said actuation means into a predetermined initial position.

9. Milk pump as claimed in claim 1, wherein said support are cap-shaped and cover said displacement space.

10. Milk pump as claimed in claim 1, further comprising an overflow valve positioned before said opening at the side of said breast hood.

11. Milk pump as claimed in claim 1, wherein at least said peripheral wall of said wall and said support are of differing materials.

12. Milk pump as claimed in claim 11, wherein at least said peripheral wall of said wall is of a material of a smaller frictional coefficient than the material of said support.

13. Milk pump as claimed in claim 11, wherein the material of said support is higher in at least one characteristic of strength and hardness than at least said peripheral wall of said wall.

14. Milk pump as claimed in claim 11, wherein at least said peripheral wall of said wall is selected of polyethylene and polyamide.

15. Milk pump as claimed in claim 11, wherein the material of said support is selected of polycarbonate and polypropylene.

16. Milk pump as claimed in claim 1, wherein said suction unit comprises a piston moveable in and along said displacement space.

17. Milk pump as claimed in claim 1, wherein said suction unit comprises a pot-shaped membrane moveable in and along said displacement space.

18. Milk pump as claimed in claim 1, further comprising a sealing arrangement between said support and at least part of said wall latched to said support.

19. Milk pump as claimed in claim 18, wherein said sealing arrangement comprises a plug connection including an externally conical pipe socket on a selected one of said support and at least part of said wall latched to said support, and a channel to receive said pipe socket.

20. Milk pump as claimed in claim 19, wherein said channel is internally conical so as to be at least substantially complementary to said externally conical pipe socket.

21. A milk pump for pumping milk from a woman's breast, comprising:
- a breast hood for receiving a woman's breast;
- a support;
- an opening in said support for providing a suction communication to said breast hood, said opening having a first longitudinal axis;
- a wall forming and surrounding a displacement space, said displacement space defining a second longitudinal axis not parallel with the first longitudinal axis and having a predetermined cross-sectional dimension, said wall comprising a front wall of said displacement space and a peripheral wall extending in a longitudinal direction along the second longitudinal axis;
- a suction unit displaceable in said displacement space substantially along the second longitudinal axis to provide suction through said opening;
- an actuator for mechanically displacing said suction unit substantially along the second longitudinal axis by pivoting about the first longitudinal axis;
- pivoting impeding means for ensuring a certain relative position of said actuator relative to said support;
- a latch formed on said front wall for releasably connecting at least part of said wall to said support wherein the latch comprises at least one protrusion from the front wall in the lateral direction and the support includes a receiving plate to receive and engage the front wall, and a locking eccentric piece or cam for cooperation with the at least one protrusion to press it against the receiving plate.

22. Milk pump as claimed in claim 21, wherein said pivoting impeding means comprises fixing means for fixing said relative position and, thus, to prevent any pivoting.

23. Milk pump as claimed in claim 21, wherein said pivoting impeding means comprises pivot limiting means for limiting pivoting over a predetermined angle.

24. Milk pump as claimed in claim 23, wherein said pivot limiting means comprises a series of catches distributed over said predetermined angle to be able to stop said actuator in a desired relative position.

25. Milk pump as claimed in claim 21, wherein said manual pumping unit comprises a return spring for returning said actuator into a predetermined initial position, said return spring having a free end, and said pivoting impeding means comprises a slot for receiving said free end.

26. A pump comprising:
- a hood;
- a collector connected with the hood for receiving liquid, the collector including:
- a support having an opening in suction communication with said hood;
- a manual pumping unit including:
  - a substantially rigid wall forming and surrounding a displacement space, said displacement space defining a longitudinal axis and having a predetermined cross-sectional dimension, said wall comprising a front wall of said displacement space and a peripheral wall extending in a direction of the longitudinal axis;
  - a suction unit displaceable in said displacement space substantially along said longitudinal axis to provide suction through said opening; and
  - an actuator for mechanically displacing said suction unit substantially along the longitudinal axis;
  - a latch formed on said front wall for releasably connecting at least part of said wall to said support wherein the latch comprises at least one protrusion from the front wall in the longitudinal direction and the support includes a receiving plate including respective openings for the at least one protrusion and wherein the latch includes at least one protrusion from the front wall in the lateral direction and the support includes a receiving plate to receive and engage the front wall, and pressure exerting means for cooperation with the at least one protrusion to press it against the receiving plate.

27. A pump according to claims 26, wherein the manual pumping unit is configured to pivot about a longitudinal axis of said opening; and
- pivoting impeding means for impeding pivoting of said actuator relative to said support, wherein said latch releasably connects said pivot impeding means with said support.

28. Pump as claimed in claim 26, further comprising a sealing arrangement between said support and at least part of said wall latched to said support.

29. A milk pump for pumping milk from a woman's breast, comprising:
- a breast hood for receiving a woman's breast;
- a support;
- an opening in said support for providing a suction communication to said breast hood, said opening having a longitudinal axis;
- a wall forming and surrounding a displacement space, said displacement space defining a longitudinal axis and having a predetermined cross-sectional dimension, said wall comprising a front wall of said displacement space and a peripheral wall extending in a longitudinal direction;
- a suction unit displaceable in said displacement space substantially along said longitudinal axis to provide suction through said opening;
- an actuator for mechanically displacing said suction unit substantially in an axial direction by pivoting about the longitudinal axis of the opening;
- pivoting impeding means for ensuring a certain relative position of said actuator relative to said support;
- a latch formed on said front wall for releasably connecting at least part of said wall to said support wherein said latch comprises at least one protrusion from the front wall in the lateral direction and the support includes a receiving plate to receive and engage the front wall, and a locking eccentric piece or cam for cooperation with the at least one protrusion to press it against the receiving plate; and
- wherein said actuator comprises a return spring for returning said actuator means into a predetermined initial position, said return spring having a free end, and said pivoting impeding means comprises a slot for receiving said free end.

* * * * *